United States Patent [19]
Klaus

[11] Patent Number: 5,408,890
[45] Date of Patent: Apr. 25, 1995

[54] PORTABLE SAMPLING APPARATUS

[76] Inventor: Bruno G. Klaus, Le Dally, 1628 Vuadens, Switzerland

[21] Appl. No.: 958,239

[22] Filed: Oct. 8, 1992

[51] Int. Cl.$^6$ .............................................. G01N 1/00
[52] U.S. Cl. ............................. 73/863.81; 73/863.85; 73/863.86; 73/864.15
[58] Field of Search ........... 73/863.71, 863.81, 863.82, 73/863.85, 863.86, 864.15, 864.63

[56] References Cited

U.S. PATENT DOCUMENTS

| | | | |
|---|---|---|---|
| 1,819,058 | 8/1931 | Arnold, Jr. ......................... | 73/863.85 |
| 1,837,858 | 12/1931 | Grace ................................. | 73/863.71 |
| 2,006,301 | 6/1935 | Meyer ................................ | 73/863.85 |
| 4,305,279 | 12/1981 | Ontek ................................ | 73/864.63 |
| 4,367,657 | 1/1983 | Ward ................................. | 73/864.65 |
| 4,454,774 | 6/1984 | Pridgen ............................ | 73/863.81 |
| 4,590,810 | 5/1986 | Hunkin et al. .................... | 73/863.71 |
| 4,628,749 | 12/1986 | Rafter, Jr. ......................... | 73/863.71 |
| 4,631,961 | 12/1986 | Yohe et al. ........................ | 73/863.85 |
| 4,986,138 | 1/1991 | Spencer ............................ | 73/863.86 |
| 5,139,654 | 8/1992 | Carpenter ........................ | 73/864.63 |

FOREIGN PATENT DOCUMENTS

| | | | |
|---|---|---|---|
| 2197469A | 5/1988 | United Kingdom ............ | 73/863.86 |
| 1318834 | 6/1987 | U.S.S.R. .......................... | 73/863.86 |

OTHER PUBLICATIONS

UTI-GT-OPTO Sampler-GT C.2–0,5 liter.

*Primary Examiner*—Richard F. Chilcot, Jr.
*Assistant Examiner*—George M. Dombroske
*Attorney, Agent, or Firm*—Griffin, Butler Whisenhunt & Kurtossy

[57] ABSTRACT

The present disclosure is directed to a method and apparatus for removing a small sized sample from a very large tanker container. The tank is closed, a valve is mounted in the deck which closes the tank, and the present apparatus attaches to that valve. This defines an open and close passage into the tank. A sample container on a measured steel tape is lowered through the passage into the tank and retrieves a measured sample. Sample container is removed outside the tank in a sample transfer mechanism. The sample transfer mechanism incorporates a container filling head or assembly which features a pair of needles which penetrate the septum on the mouth of a half liter or liter container which can be carried to a test facility after filling. Two needles are used, one to introduce the liquid into the container and the other to vent the container fumes or any over flow, and the vented fumes and over flow are directed to a charcoal carbon filled filter.

19 Claims, 4 Drawing Sheets

PORTABLE SAMPLING APPARATUS

BACKGROUND OF THE DISCLOSURE

The present disclosure is directed to an apparatus for removing a sample from a liquid storage container such as a hold below the deck of a tanker or the top or cover of a fixed tank for receiving and storing thousands of gallons of a liquid product. Also, it can be moved from one tank to the next, both ship board or at fixed tanks in a tank yard or the like. Examples will be used below including barges, tanks and ships. The liquid products are typically subject to vaporization. Indeed, they may be formed of many constituent components so that there is a tendency of the liquid in the storage container to vaporize when exposed to the atmosphere. The several constituents may have different vapor pressures. Some may vaporize quite readily and others may vaporize rather slowly, or perhaps not at all. As a generalization, these products are described as petrochemical products. They are normally valuable products but they are not freely vented to the atmosphere for vaporization. Moreover, such products have to be sampled, tested, measured and assayed. It is not uncommon for the tank of a large vessel to be quite deep, perhaps as much as 100 feet in depth, or about 30 meters. It is not uncommon for the storage compartment of a tanker to be 10 meters in length. The petrochemical cargo which is placed in such a large tank or container can be very large and can fill the storage container almost to the top of the container. In these situations, it is necessary to make periodic measurements to test or check the cargo in the tanker to assure that a product is delivered which has a known purity. The device of this disclosure is a measuring apparatus which can be used to take a sample from a closed tank aboard a vessel. More importantly, it is a device which can take a sample from a controlled depth in a tank. Consider the example of an ocean going vessel which has a large storage tank of 30 meters in depth normally used to haul petrochemical products. As a generalization, the bottom of the tank will collect a layer of sediment and typically also a thin layer of water will collect on top of the sediment. The sediment will settle to the bottom of the tank by virtue of the relative difference in the weight of the materials. The water will settle to the bottom of the tank also because it is normally heavier than most petrochemical products. Most of the time, the petrochemical product placed in the tank will float on the water. More than that, it may stratify by separating into constituent components. For instance if a cargo is shipped on a transatlantic passage, it may stay in the tank of the vessel for perhaps 10 to 20 days depending on the delays encountered in loading and off loading. During that interval and dependent on the agitation of the tank, the cargo may stratify into two or three different layers. On arrival at a port after such a transatlantic voyage, it may be necessary to remove samples from the tank. It is extremely important to remove samples from a controlled depth. The depth normally is known because it is intimately connected with the vessel size and is the type of data which is always available.

The present apparatus is directed to a sample removal system which can be connected with a tank to remove a calibrated sample volume from a specified depth. For instance, if a sample of the sediment and water at the bottom of the tank is desired, the device of the present disclosure includes a sample container which is lowered into the tank to the bottom. Normally, the clearance between the top of the tank and the bottom of the tank is well known in advance. If it is suspected that the petrochemical cargo has stratified into several layers, different samples can be taken from different depths. In each instance, a small container is lowered to a desired depth and then is retrieved on a measuring tape or line. The measuring tape is calibrated so that the depth of the measuring instrument and container is known. Moreover, this procedure enables the testing of the materials by retrieval from the tank and subsequent transmission to a laboratory.

It is not enough merely to retrieve a sample container of liquid from a tank. While the container is small for instance, one liter or less, there is always the difficulty of getting the liquid out of the container and into another container for easy transportation to a remote facility for testing. More than that, there is always the possibility that the retrieved liquid cargo may well further be changed by loss of light vapor constituents. These typically are the lighter molecules which have substantial value in the product, and which vaporize too readily. This can include dangerous constituents such as benzene which is regulated severely for its escape into the atmosphere. This also can include the lighter constituents of the common constituents, namely, gasoline such as the $C_4$, $C_5$, $C_6$, etc. components. The present apparatus is a system which enables test personnel to retrieve a liquid sample from a tank without releasing fumes to the atmosphere, and without spilling liquid. It is a system which permits the sample measuring container to be lowered down into the tank and into the liquid cargo for retrieval of a sample or specimen from a determined depth. Moreover, the entire process of lowering the container into the liquid cargo and making retrieval is accomplished in a closed vessel so that there are no fumes permitted to escape to the atmosphere. An important feature of the present apparatus is the ability of the equipment to readily remove a measured sample and to subsequently transfer the sample from the equipment into a septum closed bottle which can then be transported easily and readily to a test facility without escape of fumes, and also without risk of spilling the contents of the bottle. Furthermore, the system includes a means and a mechanism whereby the sample which is retrieved can be delivered into a sized measuring bottle for easy transportation to a test laboratory and the like. Indeed, the present apparatus is a system which, when considering the taking of samples from a tank which is 30 meters in depth, can readily obtain 6 or 8 samples in separate bottles, each sealed against leakage, and each prepared for immediate transportation to a laboratory. All of this can be obtained at a single site on the top of the decking or structure which defines the deep tank, and all of this can be accomplished readily with minimal vapor escape to the atmosphere.

The present apparatus is summarized as a permanently installed ball valve including a quarter turn rotating trunnion and shaft which positions the valve so that a vertical passage through the valve into the tank is defined. It is typically mounted on the deck over a tank. The ball valve is closed ordinarily, but, on quarter turn rotation, the ball is moved to an aligned position so that a vertical passage through the ball valve is opened. The ball valve connects with an open ended upper port. By means of a suitable fitting, an upstanding sampler column is positioned over that. It is elongate and hollow, defining a double wall. It is sufficiently tall that it receives and holds a sample container. This sample container is weighted at the bottom so it hangs upright. At the top end, it has a hook or eyelet which enables it to be connected with an elongate measuring tape. The sample container is lowered downwardly through the open ball valve and into the tank. The sample container is constructed to receive and hold a sized sample. Moreover, the upstanding hollow column which defines the equipment includes an over head storage reel or drum which holds the several bights of an elongate steel measuring tape. It is calibrated to an adequate length to assure that the sample container is lowered to any depth in the tank. The upper end of the upstanding sampler test equipment is equipped with a fitting which enables introduction of nitrogen under pressure. The air or nitrogen under pressure is forced downwardly into the apparatus and provides a fluid drive for urging the liquid from the storage container. Sample is forced downwardly and flows into an annular space defined by a double wall construction. Sample must flow upwardly through the double wall space to the top end of the annular space between the double walled construction. The liquid is driven out through a fitting. It then flows into a control valve. This valve is operative to provide fluid flow downwardly through the first needle of a pair of needles which are inserted through a septum covering over the mouth of a small sample bottle. The bottle is filled by flow through this route but there is also an outlet passage from the bottle through a second needle. When overflowing or expelling air, this flows through a controlled pathway into a disposable filter in a container which is filled with charcoal or some other particulate carbon product for filtration. In turn, any discharge then flows into an outlet conduit. The fluid flow is under power of either nitrogen introduced to push the liquid out of the system, or, in the alternative, fluid flow is initiated by provision of a vacuum pump at the outlet end (pulling the vapors through a carbon filter). The present apparatus thus enables a sample to be retrieved from a large tank holding great quantities of a petrochemical product and delivery of a specified size of sample into a sample container, and all of this is accomplished substantially without permitting fumes to escape to atmosphere.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DESCRIPTION OF THE PREFERRED AND ILLUSTRATED EMBODIMENTS

Figure 1:
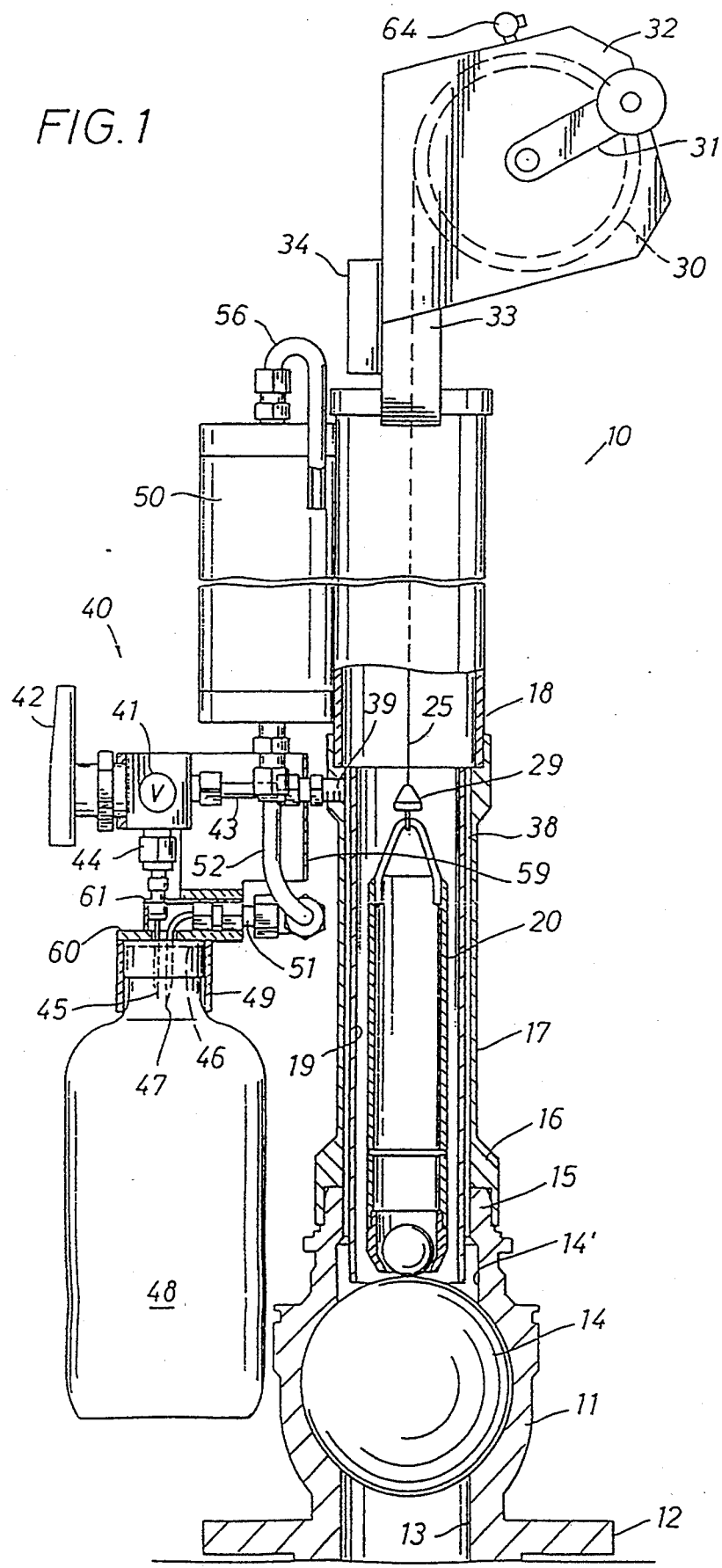
FIG. 1 is a side view of the sample retrieval apparatus of the present disclosure where part of the upstanding cylindrical portion has been broken away and is shown in sectional view wherein the equipment connects above a tank for retrieving one or more samples from the tank.

Attention is now directed to FIG. 1 of the drawings where the numeral 10 identifies the sample collection system of the present disclosure. It will be described proceeding from the bottom of the equipment. The system is best understood in the installed condition on a tanker or barge. To that end the system is provided with a ball valve mechanism which is installed at an opening into the tank. This defines the point of access to a particular storage tank. If desired, one tank can have several valves over it but one is usually sufficient. More particularly, the numeral 11 identifies a valve housing which is mounted on a flange 12 which is readily fastened to or connected with the deck over the top of a tank. The tank is typically covered and closed for ocean borne transportation. The tank is affixed to the flange by suitable bolts or rivets which fasten the flange at a particular location. The flange supports the ball housing 11. The ball housing defines a vertical passage having an inlet 13 which opens to a specified diameter and which is vertically aligned. Moreover, the housing 11 encloses a ball valve element 14. It is positioned to open or close a fluid pathway from the inlet port 13 through an outlet port 14'. Typically, the ball 14 is mounted on a trunnion which enables the ball to be rotated by 90° between the open and closed positions. The trunnion extends from the housing 11 and normally supports a lever or handle which is grasped by the operator and is rotated to thereby rotate the ball to one position or the other. When the valve is open, there is a pathway that extends vertically in alignment with the inlet port 13 and the outlet port 14'. This pathway is sized to a dimension which permits entry of a sample container which will be detailed momentarily.

Figure 2:
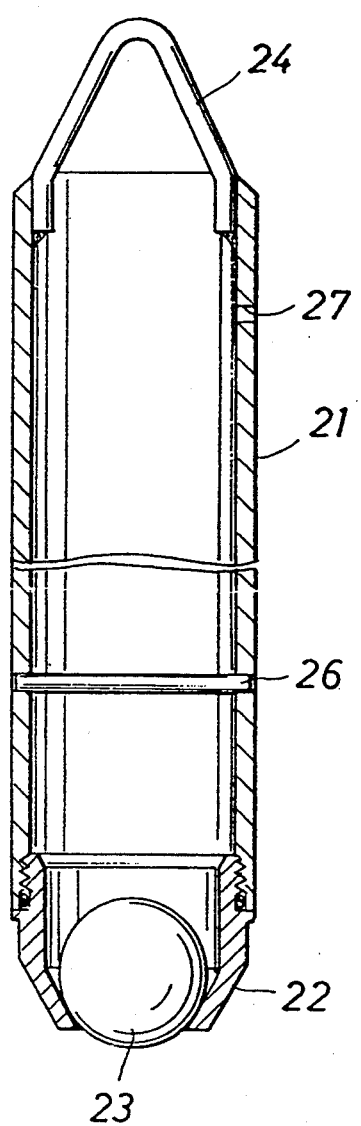
FIG. 2 is a sectional view through a sample container used to retrieve a small sample from the tank.

The housing 11 terminates at an upstanding skirt 15 which connects with a quarter turn twist lock connector 16 which is joined to and part of an upstanding external sleeve 17. The sleeve 17 in turn connects with a longer cylindrical member 18 which thereby extends the structure to a defined height. Further, the upstanding cylindrical member 17 is on the exterior of and spaced from an internal sleeve 19. The two sleeves define a central passage which is aligned with the ball valve 14 below. This defines a pathway through which a sample container 20 can be moved. The sample container 20 is constructed for movement into and through the ball valve 14. It has a diameter which is sufficiently small to enable the sample container 20 to be dropped into the tank for making a measurement. The sample container is sized to hold a specified internal volume. The sample container 20 is better defined in FIG. 2 of the drawings. There, it is shown to include an upstanding hollow cylinder 21 which is open at the top and bottom. At the bottom, there is a fitting 22 which is slightly tapered inwardly to serve as a check valve seat. A check valve element 23 having the form of a sphere in the preferred embodiment closes the bottom. The check valve element 23 is sufficiently heavy that it falls to the bottom for closure. As desired, the check valve 23 is held in the cylinder so that it will not escape. This can be assured by means of an upstanding eyelet 24 arranged at the upper end of the device. This enables connection to a line 25 which will be detailed later. Alternately, a pin 26 can be fastened across the container so that the valve element 23 does not escape.

In the preferred embodiment of the present disclosure, the sample container has a small opening 27. This defines the amount of liquid that is stored in the sample container. The small port or weep hole 27 is located at a height which defines the sample capacity. It can be omitted and the top edge of the container will serve the same purpose assuming it is cut to a desired height. The sample container measures a specific volume of material such as one liter, or perhaps one half liter. This is the amount of liquid which is captured below the weep hole 27 and above the check valve element 23. As mentioned, the volume can be modified by drilling the weep hole 27 at a different location. Another modification involves placing several holes 27 in the side of the apparatus and selectively plugging all of them except one which then defines the storage capacity of the container. If desired, the container can measure only a single volume simply by omitting the hole 27 and filling to the top of the container. In many instances, that will be acceptable because the sample sizes are required to be a specified volume and the container is shaped or defined to that particular volume.

Going back to FIG. 1 of the drawings, the measuring tape 25 attaches by a suitable swivel 29 to the eyelet 24. The tape 25 is a measuring tape of relatively thin gage metal but which has the form of a steel strap with a coated steel surface so that it does not corrode. It is protected against rust also. It is a tape on which distances are imprinted so that it serves as a precisely defined measuring tape. The tape is extended upwardly through the apparatus shown in FIG. 1 and spools about a storage drum 30 which is indicated in dotted line in FIG. 1. The storage drum 30 is rotated by a hand crank 31 which is easily engaged by the hand of a user to thereby extend or retract the steel tape 25. The tape is extended or retrieved by hand operation. It is generally desirable that the tape pass through a pair of rollers which tend to wipe away any liquid which may cling to the surface of the tape. The tape is then stored around the drum or reel 30. The reel is enclosed within a metal housing 32 which is supported on an upstanding support arm 33. The arm 33 aligns the reel 30 so that the steel tape extends downwardly. The steel tape is calibrated so that it can be viewed through a window 34. The steel tape is marked with suitable increments of distance on the face of the tape which permit reading of the steel tape. The steel tape therefore enables the operator to raise and lower the sample container 20.

SAMPLE COLLECTION

Consider the following sequence of operations in removing a sample from the tank. Normally, the ball valve 14 is rotated to a position which closes the valve element and passage. Typically, some type of protective cover is placed over the upper end of the valve mechanism. The exposed upper end is then located, thereby enabling the upstanding equipment shown in FIG. 1 and indicated by the numeral 10 to be quickly attached to the skirt 15. Once attachment is made for the sample 10, the valve element 14 can then be opened by rotation. It is rotated so that a passage is defined for the sample container 20 which permits the sample container to pass through the ball valve. As illustrated in the full line position of FIG. 1, the check valve element 23 is exposed where it can be dislodged, that is, where it can be bumped and dislocated from the closed position. In any event, this equipment is installed so that the sample container 20 is just above the rotatable valve element 14. This then permits the equipment 10 to be connected above the valve element 14, the steel tape 25 extended by hand operation of the crank 31, thereby lowering the sample container 20 and extending the steel tape downwardly through the valve element passage so that the sample container 20 is located in the tank at the desired depth. Once the sample container is lowered to the required depth, a sample is captured in it and held in it in the fashion of a bucket or other container. The sample is then removed in the sample container which functions as a liquid cup or bucket. This permits the sample container to be filled from a desired depth and then raised back through the valve element 14. The sample container can be pulled sufficiently high in the equipment 10 that it clears the valve element 14. Moreover, after it clears, the operator can then close the valve element 14 so that the passage is no longer available. This captures any liquid which is above the ball valve element 14. At this juncture, the measured liquid sample remains in the sample container, but when the sample container is lowered by slightly extending the steel tape 25, the liquid in the sample container escapes because the check valve element 23 is dislodged from its seat (see FIG. 2). When that occurs, any liquid in the sample container flows downwardly into the outlet port 14' and is collected on top of the ball valve element 14. While it has not been categorically stated, it is assumed that the ball valve 14 cooperates with a set of seals (not shown) which assure that there is no leakage out of the equipment back into the tank below the ball valve element 14. Any liquid remaining on the ball valve element is held there until the ball valve is opened and fill flow back into the tank.

From the foregoing, retrieval of liquid is understood as a result of this explanation. However, another step remains, namely removal of the measured and retrieved liquid. Ideally, the retrieved liquid is placed in a sample bottle and is removed for a test laboratory. Equipment will be further described which carries out this step part of the process.

There is an annular cavity which is between the two cylindrical members 17 and 19. This cavity is a narrow annular space which is identified by the numeral 38. A sample filling apparatus 40 is attached at this location by means of a fitting 39. The fitting 39 provides a lateral liquid flow path to a filling valve 41. The valve 41 is operated by a hand operated handle 42. The fitting 39 connects serially from that location through a tubing 43 which is input to the valve element 41. A liquid flow path is defined from the valve element 41 downwardly through another fitting 44 and then through a needle 45 which is inserted through a transverse septum 46 which closes the top of a sample bottle 48. Assume for easy illustration that the sample container or bottle 48 receives and stores 500 ml of sample. It is closed by means of the septum 46, and further closure is assured by a removable cap (not shown). The bottle is stabbed upwardly into a surrounding ring 49 which aligns the bottle. The bottle is stabbed upwardly and the needle 45 relatively stabs through the septum 46. This provides a liquid pathway into the bottle for filling the bottle. The annular space 38 between the cylinders 17 and 19 is relatively short to limit liquid accumulation in that region which typically collects as small droplets on the two walls.

In addition, the bottle is provided with a second flow path incorporating a second needle 47. The needle 47 is parallel to and similar to the needle 45 just mentioned. The two needles serve as means for filling and emptying the sample storage bottle 48. More particularly, the needle 47 is a bent needle and connects with a laterally directed fitting, the lateral fitting also providing a connective fluid flow pathway into an absorbent filter 50. The filter 50 is attached by means of a strap which extends around the filter housing and secures it around the upright cylindrical member 18. In addition, the cartridge 50 is provided with vapor flow input at the bottom. This is through a pathway extending from the bent needle 47 through a lateral flow line 51 which in turn connects with another upstanding flow line 52. The flow line 52 is aligned with and directed toward the center line axis of the cartridge 50. The cartridge 50 is preferably an elongate cylindrical cartridge filled with particulate material. The cartridge 50 is incorporated to absorb all surplus flowing out of the sample container 48 to assure that spillage does not occur and that fumes are not vented to atmosphere. Some liquid, usually a small amount, will reach the filter as a result of vapor condensation or a result of minor volumetric differences relating to the container 20 and the container 48.

SAMPLE TRANSFER PROCEDURE

The liquid flow path including the sample collection assembly just mentioned incorporates or begins with the annular space 38 and is then directed to the fitting 39. It flows horizontally through the supply line 43 to the control valve 41. If the valve is closed, there is no flow; however, flow is normally permitted and the flow is directed downwardly from the valve 41 flowing through the fitting 44 and into the needle 45 which punctures the septum on the storage container 48. Air in the container 48 (and any other gases, fumes or liquids) is forced out of the container 48 as it is filled, and that flow is into the needle 47, then through the fitting 51, then vertically through the tubing 52 and into the filter container 50. From the latter, any condensate liquid or filtered gas emerging from the filter container 50 flows out through an inverted tube 56 which is attached at the top end of the filter container 50. Some vapors will condense in the filter 50 or elsewhere in the test apparatus. For example, if the tank is aboard a ship sailing from a hot region, the cargo will be warm and more readily vaporize. As the vessel sails into a cooler region, the vapors will more readily condense as a result of the cooler air.

The various fittings just mentioned are supported on a mounting bracket 59 which connects with a pair of horizontal support members 60 and 61. They are joined together to define a supportive frame work. Collectively, the bracket 59 and the components 60 and 61 are secured by an elongate strap which extends around the upstanding hollow cylindrical member 17 but which has been omitted for sake of clarity of the drawing. The bracket 59 also incorporates a suitable supportive front plate which holds the valve 41 in place. This permits the handle 42 to be attached to the valve for rotation. Typically, the handle is rotated by a quarter turn from the opened to the closed condition.

The liquid flow path in the equipment just mentioned requires that the liquid from the sample container 20 be delivered out of the sample container but to a location above the ball valve element 14. By use of a fitting 64, gaseous nitrogen can be forced into the closed cylindrical sleeve 19 there below to flush the liquid which is captured above the valve element 14. It is forced to flow upwardly. It flows upwardly in the annular space 38 and will flow to the fitting 39 where it is delivered laterally into the conduit 43. The liquid is delivered through the valve 41 which is assumed to be open. Liquid sample flows downwardly through the needle 45 into the container 48 which has been properly connected. This fills the bottle. Air and vapors in the bottle 48 are forced out of the bottle through the needle 47 and upwardly through the lines 51 and 52 into the filter 50. The flow is directed into the filter 50 and then flows through the U-shaped tube 56 into the atmosphere. The measured quantity of liquid from the sample container 20 is delivered into the bottle 48 which is filled to its liquid capacity. If over filled, a modest amount of liquid will be forced out of the bottle and possibly into the cartridge filter 50. Generally speaking, it is not desirable to do this but the filter material in the cartridge 50 will typically absorb the liquid so that it does not escape to atmosphere and does not dribble or leak back into the container 48. This assures that the sample which was delivered through the sample container 20 does not escape to atmosphere. Rather, all the liquids and gases captured in the system must flow through the particulate filter 50, and the atmosphere is substantially protected against the escape of vapors from the liquid sample. The vapors are primarily absorbed. The annular space 38 is preferably shortened to reduce droplet accumulation and the liquid volume dripping downwardly to accumulate on the ball valve element 14 in the equipment. The valve element 14 is opened and closed to remove surplus liquid. If desired, a purge gas flow can be introduced to remove any droplets above the valve element 14. The nitrogen gas drive can be used as a purge gas flow to clear the test equipment 10. After each use, the gas purge can be done. Indeed, the fitting 64 can be located above the drum or reel 30 to flow dry nitrogen downwardly around the tape to help remove droplets on the measuring tape.

ALTERNATE EMBODIMENTS

Figure 3:
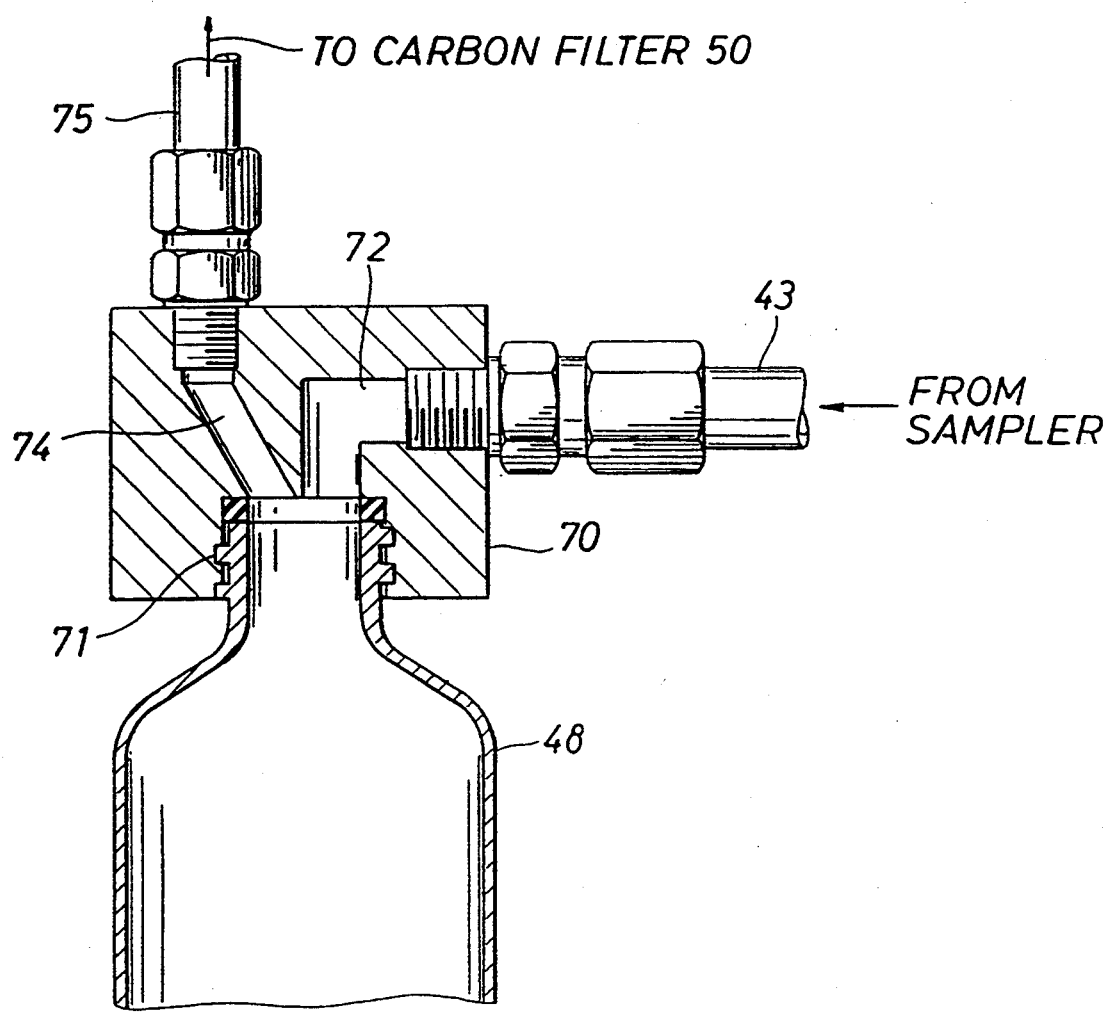
FIG. 3 shows an alternate bottle construction along with an alternate filling mechanism which enables a heavy viscous material to be delivered into the sample storage bottle.

Going now to FIG. 3 of the drawings, the sample bottle 48 is again shown but the septum has been omitted. In this instance, there is a manifold block 70 which has a set of internal threads 71 which enable the bottle to be threaded into it. The manifold block has a first passage 72 which connects with the flow line 44 previously shown in FIG. 1 of the drawings. In addition, there is a flow path in the second passage ultimately leading to the charcoal carbon filter 50. Connective lines and valves are omitted for sake of clarity. The line 75 extends to the carbon filled filter 50. The embodiment shown in FIG. 3 is especially useful when the liquid is sufficiently viscous that it will not readily flow. In that instance, it will not flow through the two needle system which delivers the liquid into the storage container or bottle 48. This is especially useful for very heavy crude oils and the like. It is also important to note that when heavy liquids are transferred into the sample bottle 48, they are typically heavy because they are formed of constituents which are not volatile. Therefore, the escape of fumes and gases to atmosphere is significantly limited.

Figure 4:
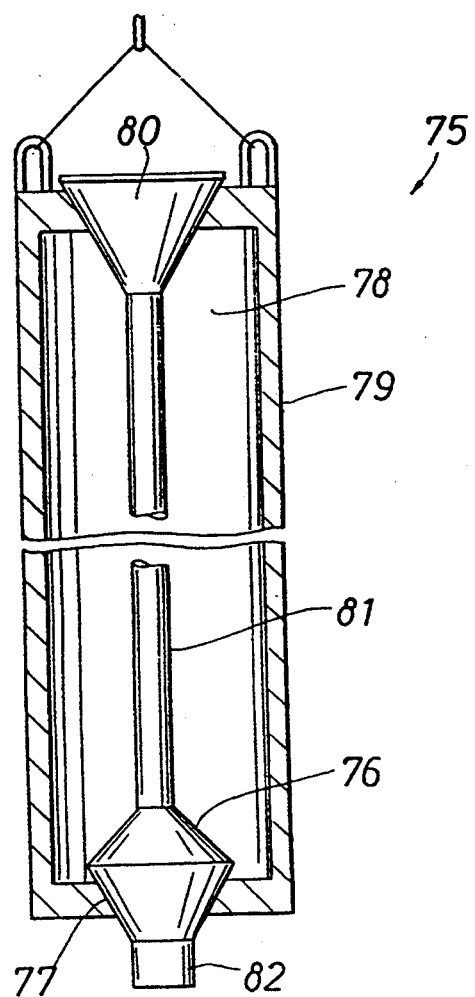
FIG. 4 is an alternate view showing another mode of construction of the sample container which particularly includes a positive closure mechanism so that sample is not permitted to escape during movement of the sample container.

Going now to FIG. 4 of the drawings, a modified sample container is indicated by the numeral 75. It includes a check valve element 76 at the bottom which cooperates with a seat 77. The seat is closed by the check valve element in the down position as illustrated in FIG. 4. There is a chamber 78 on the interior which is calibrated to a particular size. The chamber, on the interior of the housing 79 is filled to a desired level. Filling is accomplished by dislocation of the check valve element 76. It opens a valve element 80 which is pushed upwardly by a connective push rod 81. The two valve elements open jointly and close jointly. The chamber 78 is filled when both are open and is closed simultaneously by movement of both to the full line position shown in FIG. 4 of the drawings. This assures that sample which is received into the chamber 78 does not normally escape. Moreover, the check valve element 76 incorporates a protruding button 82 which is bumped or dislodged to assure opening at the desired time. For instance, it can be opened by relative movement of the sample container 75 shown in FIG. 4 against the ball valve element 14 shown in FIG. 1 of the drawings. If the apparatus 75 were substituted into FIG. 1, it would operate in that fashion to assure positive collection of a sample without commingling during retrieval.

If desired, the manifold of FIG. 1 and the valve 41 shown there can be a two way, four port valve. In this arrangement, the four ports would connect to the first needle, the second needle, the filter 50 and the liquid supply line 43. In the transfer mode, the supply line 43 would connect to the liquid input needle while the vapor removal needle would direct flow to the filter 50. On rotation of 90° as described, the line 43 would deliver all vapors from the test device 10 into the filter 50.

While the foregoing is directed to the preferred embodiment, the scope thereof is determined by the claims which follow:

It is claimed:

1. A sample system for removing a sample from a large tank comprising:
   (a) an sample container;
   (b) an elongated tape connected to said sample container for lowering the sample container into the tank and then raising the sample container from the tank to thereby collect and hold a sample of a liquid in the tank;
   (c) tank mounting means enabling said sample container to be moved into and from the tank, said tank mounting means having an internal member through which the sample container can be moved and an external member spaced from the internal member to form a transferring cavity; and
   (d) sample transferring means connected to said tank mounting means for transferring via said transferring cavity a collected sample of liquid into a liquid sample container.

2. The sample system of claim 1 wherein said sample container comprises an upstanding, open top container having a check valve at the bottom thereof wherein said check valve has a check valve element protruding therefrom which enables sample container discharge by movement of said check valve element.

3. The sample system of claim 1 wherein said elongated tape is spooled on a storage reel connected with a hand crank to enable said elongated tape to be extended, and further wherein said elongated tape incorporates calibrations thereon to determine the distance by which said sample container is raised and lowered into a tank.

4. The sample system of claim 1 wherein said sample transferring means comprises a liquid flow passage connected with said transferring cavity and further includes:
   (a) a valve connected to said passage;
   (b) means connected from said valve into a liquid sample container filling spigot;
   (c) seal means for temporarily sealing said liquid sample container during filling; and
   (d) means for controllably venting said liquid sample container during filling into a filter means.

5. The sample system of claim 4 wherein said sample transferring means further includes first and second needles which are adapted to extend into said liquid sample container, and said liquid sample container is constructed with a flexible septum over the top thereof which is penetrated by a needle enabling insertion into said liquid sample container for delivery of sample into said liquid sample container.

6. The sample system of claim 4 including an alignment collar for said liquid sample container.

7. The sample system of claim 4 wherein said venting means connects from said liquid sample container through a needle having a tip inserted into said container and extending to said filter means.

8. The sample system of claim 7 wherein said filter means is a vertically positioned elongate cylinder having a vent at the top thereof.

9. The sample system of claim 8 wherein said elongate cylinder encloses a charcoal filter material.

10. The apparatus as claimed in claim 1 wherein said internal member and said external member are both cylindrical sleeves and said cavity is a narrow annular space.

11. A method of removing a measured liquid sample comprising the steps of:
   (a) sinking a sample container to a selected depth in a tank of stored liquid to fill the sample container with a sample;
   (b) moving the sample container, after filling, out of the tank which stores the liquid and into a sample transfer means to enable discharge of said sample from said sample container in said sample transfer means;
   (c) discharging the sample from said sample container into the sample transfer means; and
   (d) subsequent to discharging the sample container, temporarily connecting a sized container with said sample transfer means and applying pressure to the discharged sample to transfer a sized sample of the liquid into the sized container, and then removing said sized container.

12. The method of claim 11 wherein said sample transfer means is:
   (a) connected with the tank which stores the liquid;
   (b) is opened to enable said sample container to be moved from said sample transfer means into the tank; and
   (c) is closed after moving the filled sample container into said sample transfer means.

13. The method of claim 11 including the step of making the transfer of liquid from said sample transfer means by placing a septum over said sized container, and puncturing the septum with a needle so that liquid is transferred from said sample transfer means through said needle into said sized container.

14. The method of claim 13 wherein said sample transfer means includes two needles wherein one of the needles is for transfer of liquid sample from said sample transfer means into said sized container, and the other needle forms a vent passage from said sized container, and thereafter venting said sized container during filling.

15. The method of claim 11 including the step of initially sealing the tank, then forming an opening into the tank and placing said sample container in said tank for sinking into the liquid to enable filling of said sized container.

16. A sample system for removing a sample from a large tank, said system comprising:
- an inlet in said tank having valve means therein for selectively opening or closing said inlet;
- a sample container;
- a tank mounting means mountable over said inlet and comprising an internal member for receiving said sample container and an external member surrounding said internal member and spaced therefrom so as to define a sample transfer cavity when said inlet is closed;
- raising and lowering means on said tank mounting means for lowering said sample container into said tank through said valve means when said inlet is open to collect a liquid sample of a liquid in said tank, and raising said sample container with a liquid sample therein into said internal member;
- means for discharging the liquid sample from said sample container into said sample transfer cavity while said sample container is inside said internal member and said inlet is closed; and,
- means for applying pressure to said sample transfer cavity to cause the discharged liquid sample to flow from said sample transfer cavity to a further container external of said mounting means.

17. A sample system as claimed in claim 16 and further comprising container mounting means for mounting said further container, said container mounting means having thereon a first connection through which the discharged liquid sample flows to said further container, said container mounting means including a second connection with said further container forming a vent passage from said further container directing vented fumes through a filter means.

18. The sample system of claim 17 wherein said first and second connections comprise a pair of parallel needles having pointed tips enabling insertion through a septum closing said further container.

19. The sample system of claim 18 wherein said further container includes a septum over a mouth on a sized sample container, and said sized sample container is closed by a cap.

* * * * *

UNITED STATES PATENT AND TRADEMARK OFFICE
CERTIFICATE OF CORRECTION

PATENT NO. : 5,408,890
DATED : April 25, 1995
INVENTOR(S) : Bruno G. Klaus

It is certified that error appears in the above-indentified patent and that said Letters Patent is hereby corrected as shown below:

Title page, item "[21] Appln. No.: 958,239" should read
--[21] Appln. No.: 958,289--

Signed and Sealed this

Twenty-fourth Day of October, 1995

Attest:

BRUCE LEHMAN

Attesting Officer     Commissioner of Patents and Trademarks